(12) United States Patent
Barnhart

(10) Patent No.: US 6,410,805 B2
(45) Date of Patent: Jun. 25, 2002

(54) METHOD AND COMPOSITION FOR HYDROXYLATION OF AROMATIC SUBSTRATES

(75) Inventor: Terence Michael Barnhart, Pattersonville, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/759,503

(22) Filed: Jan. 16, 2001

Related U.S. Application Data

(62) Division of application No. 09/259,652, filed on Feb. 26, 1999, now Pat. No. 6,265,622.

(51) Int. Cl.$^7$ ............................................. C07C 37/00
(52) U.S. Cl. ...................... 568/802; 502/155; 502/160; 502/167; 502/170; 252/182.32; 252/182.33; 568/803
(58) Field of Search ................... 568/802, 803; 502/160, 167, 170, 155; 252/182.32, 182.33

(56) References Cited

U.S. PATENT DOCUMENTS

| | | | | |
|---|---|---|---|---|
| 3,445,526 A | * | 5/1969 | Hooper | 568/802 |
| 3,453,332 A | | 7/1969 | Vesely et al. | |
| 3,549,713 A | * | 12/1970 | Charman | 568/802 |
| 3,804,906 A | | 4/1974 | McAvoy | |
| 4,529,824 A | * | 7/1985 | Mimoun | 568/803 |
| 4,982,015 A | * | 1/1991 | Chao | 568/802 |
| 5,001,280 A | | 3/1991 | Gubelmann et al. | |
| 5,110,995 A | | 5/1992 | Kharitonov et al. | |
| 5,180,871 A | | 1/1993 | Matsunaga et al. | |
| 5,233,097 A | | 8/1993 | Nemeth et al. | |
| 5,426,245 A | * | 6/1995 | Hamada | 568/802 |
| 5,756,861 A | | 5/1998 | Panov et al. | |
| 5,952,532 A | | 9/1999 | Durante et al. | |

FOREIGN PATENT DOCUMENTS

| | | |
|---|---|---|
| EP | 0 638 536 | 2/1995 |
| EP | 0 885 865 | 12/1998 |

OTHER PUBLICATIONS

Miyake, Applied Catalysis A: General, vol. 131, pp. 33–42 (1995).*
Atsutaka Kunai, et al.: "Catalytic Oxidation of Benzene. Catalyst Design and Its Performance", Bulletin of the Chemical Society of Japan, vol. 62 (8), pp. 2613–2617 (1989).
Hubert Mimoun, et al.: "Vanadium (V) Peroxo Complexes. New Versatile Biomimetic Reagents for Epoxidation of Olefins and Hydroxylation of Alkanes and Aromatic Hydrocarbons", Journal of the American Chemical Society, vol. 105 (10), pp. 3101–3110 (1983).
Chemical Abstracts, "Oxidation of Methane and Benzene With Oxygen Catalyzed By Reduced Vanadium Species at 40° C.", Yamanaka, Ichiro; Morimoto, Keiji; Soma, Masanori and Otsuka, Kiyoshi, vol. 129: 188970a, p. 630 (1998). Abstract of JP 0626 242 (1994).

* cited by examiner

Primary Examiner—Michael L. Shippen
(74) Attorney, Agent, or Firm—S. Bruce Brown; Noreen C. Johnson

(57) ABSTRACT

A method and composition are disclosed for the hydroxylation of aromatic substrates in the presence of oxygen, hydrogen, and a catalyst. In a preferred embodiment, benzene is oxidized to phenol in the presence of oxygen, a vanadium catalyst, and hydrogen. The method is economical, safe, and amenable to commercial scale-up.

13 Claims, No Drawings

METHOD AND COMPOSITION FOR HYDROXYLATION OF AROMATIC SUBSTRATES

This application is a division of application Ser. No. 09/259,652, filed Feb. 26, 1999 now U.S. Pat. No. 6,265,622 which is hereby incorporated by reference in its entirety.

BACKGROUND OF THE INVENTION

This invention relates to methods for the hydroxylation of aromatic substrates. In particular, this invention relates to a method for producing hydroxyaromatic compounds by the oxidation of aromatic substrates in the presence of oxygen, hydrogen, and a catalyst. The invention also relates to catalyst compositions for effecting said hydroxylation.

Phenol is among the most important industrial organic chemical intermediates, being used for the manufacture of thermoplastics and other resins, dyestuffs, explosives, agrochemicals, and pharmaceuticals. It is particularly important in the manufacture of phenol-formaldehyde resins used in the construction, appliance, and automotive industries, and in the manufacture of bisphenol A for epoxy and polycarbonate resins.

Despite its industrial importance, prior art methods for the production of phenol are non-selective, multi-step, and/or expensive. For example, benzene may be alkylated to obtain cumene, which in turn is oxidized to form cumene hydroperoxide. The hydroperoxide is cleaved using an acid catalyst to form phenol and acetone. Another industrial process using oxidation of toluene requires expensive starting materials. Older industrial processes such as the Raschig Hooker process require high energy input, and result in corrosive or difficult to dispose of wastes.

More recent processes for the production of phenols include the hydroxylation of aromatic substrates using hydrogen peroxide in the presence of a titanoaluminate molecular sieve, as disclosed in U.S. Pat. No. 5,233,097 to Nemeth et al., or in the presence of a hydrogen fluoride-carbon dioxide complex as disclosed in U.S. Pat. No. 3,453,332 to Vesely et al. U.S. Pat. No. 5,110,995 further discloses hydroxylation of phenol or phenol derivatives in the presence of nitrous oxide and zeolite catalyst. A multistep process requiring partial hydrogenation of benzene, separation of the reaction products, oxidation of some of the reaction products, dehydrogenation, and other steps is disclosed in U.S. Pat. No. 5,180,871 to Matsunaga et al. U.S. Pat. No. 5,001,280 to Gubelmann et al., U.S. Pat. No. 5,110,995 to Kharitonov et al., and U.S. Pat. No. 5,756,861 to Panov et al. disclose oxidation of benzene to phenol by nitrous oxide in the presence of a zeolitic catalyst, with yields of up to about 16%.

While certain of these methods provide good yields, they still suffer from various drawbacks and disadvantages. In particular, nitrous oxide is expensive, and it is also a greenhouse gas that presents significant environmental concerns. Thus, despite the number of methods available to synthesize hydroxyaromatic compounds, there still remains a need for a process that is simple, high-yield, environmentally friendly, economical, and amenable to commercial scale-up.

SUMMARY OF THE INVENTION

The above-described drawbacks and disadvantages are alleviated by the method described herein, which is a method of hydroxylating an aromatic substrate, which comprises reacting an aromatic substrate having at least one active aromatic hydrogen in the presence of oxygen, hydrogen and a catalyst. The method is environmentally friendly, economical, safe, and amenable to commercial scale-up.

In another embodiment the invention comprises a catalyst composition for hydroxylating an aromatic substrate having at least one active aromatic hydrogen, comprising oxygen, hydrogen, a vanadium, niobium, or tantalum precursor or mixture thereof, at least one anionic ligand precursor, and at least one neutral, electron-donating ligand precursor.

DETAILED DESCRIPTION OF THE INVENTION

The present method is directed to hydroxylation of aromatic substrates in the presence of oxygen, hydrogen, and a catalyst. One preferred embodiment comprises hydroxylation of benzene in the presence of oxygen, hydrogen, and a vanadium catalyst.

One or more of a range of aromatic substrates may be hydroxylated in the practice of this method. Preferably the aromatic substrate is benzene, naphthalene, anthracene, phenanthrene, or the like, or substituted derivatives thereof. The substituents may be the same or different. The number of substituents may vary, as long as at least one active aromatic hydrogen is available for substitution, where an active aromatic hydrogen is one capable of being replaced by hydroxyl to produce a hydroxyaromatic compound. Benzene, for example, may have from one to five substituents, which may the same or different.

Suitable substituents include one or more aryl groups, for example phenyl, naphthyl, anthracyl, and phenanthryl. The aryl substituents may themselves be substituted by various functional groups, providing that such functional groups do not interfere with the hydroxylation. Suitable functional groups include, but are not limited to, alkyl groups as described below, carboxylic acids, carboxylic acid alkyl and aryl esters, aldehydes, hydroxyls, olefins, and alkyl and aryl ethers. Mixtures of different aryl groups and/or substituted aryl groups as substituents are also within the scope of the invention.

Other suitable substituents include one or more alkyl groups, wherein the alkyl groups are straight- or branched-chain, or cyclic, and typically have from one to twenty six carbons. Some illustrative non-limiting examples of these alkyl groups include methyl, ethyl, propyl, isopropyl, butyl, tertiary-butyl, pentyl, neopentyl, hexyl, cyclobutyl, cyclopentyl, cyclohexyl, methylcyclohexyl, cycloheptyl. Exemplary alkyl-substituted benzenes include, but are not limited to, toluene, xylene, and cumene. The alkyl groups may themselves be substituted by various functional groups, providing that such functional groups do not interfere with the hydroxylation. Suitable functional groups include, but are not limited to, aryl groups as described above, carboxylic acids, carboxylic acid alkyl and aryl esters, aldehydes, hydroxyls, olefins, and alkyl and aryl ethers. Mixtures of different alkyl groups and/or substituted alkyl groups as substituents are also within the scope of the invention.

Other suitable substituents include, but are not limited to, one or more functional groups, providing that such functional groups do not interfere with the hydroxylation. Suitable functional groups include, but are not limited to, carboxylic acids, carboxylic acid alkyl and aryl esters, aldehydes, hydroxyls, olefins, and alkyl and aryl ethers. Mixtures of different functional groups as substituents are also within the scope of the invention. Mixtures of substituents comprising combinations of functional groups, aryl groups, alkyl groups and/or their functionalized derivatives are also within the scope of the invention.

Preferred aromatic substrates are benzene, and benzene substituted by alkyl groups, aryl groups, alkyl ethers, aryl ethers, or combinations thereof. Especially preferred are biphenyl, phenyl phenol, toluene, cumene, phenol, and para-cumyl phenol.

Molecular oxygen may serve as both oxidant and source of hydroxyl oxygen in the present hydroxylation method. Hydrogen may serve as a reductant. The compositional ratio between oxygen and hydrogen is preferably outside the explosive range from the viewpoint of safety. The hydroxylation advantageously proceeds in the presence of a mixture of oxygen, hydrogen, and up to about 90% of at least one inert gas, e.g., nitrogen, argon, helium and the like. A preferred hydrogen source is molecular hydrogen, which may be used directly or in a mixture, especially, e.g., as a mixture with the oxygen source. A preferred oxygen and hydrogen source comprises air, or mixtures comprising the components of air. The partial pressure of oxygen is preferably in the range from about 0.02 megapascals (MPa) to about 7.1 MPa, and the partial pressure of hydrogen is preferably in the range from about 0.002 MPa to about 1.42 MPa. The absolute total pressure of the reaction is within the range of about 0.1 MPa to about 36 MPa, and preferably within the range of about 1 MPa to about 8 MPa.

Preferred catalysts are based on precursors which under the reaction conditions produce a catalyst effective in the hydroxylation of an active aromatic hydrogen. Such precursors include precursors giving rise to a metal complex, such as a vanadium, niobium or tantalum complex or mixtures thereof; precursors giving rise to an anionic ligand; precursors giving rise to a neutral, electron-donating ligand, and precursors comprising a combination of vanadium, niobium or tantalum with either an anionic ligand or a neutral, electron-donating ligand, or both. The anionic and/or neutral, electron-donating ligands may be present in the same molecule, for example as bidentate or tridentate ligands.

Suitable metal precursors include, but are not limited to, the oxides or the alkali metal salts of vanadium, niobium, or tantalum, for example sodium metavanadate; substituted oxides of vanadium, niobium and tantalum, for example VO(acetylacetonate)$_2$ and VO(picolinate)$_2$, and alcoholates such as tantalum trisethoxide and niobium trisethoxide. Mixtures of metal precursors are also within the scope of the invention. In particular, mixtures of precursors containing either the same or different metals are suitable.

Suitable anionic ligand precursors include, but are not limited to, halides, carboxylic acids and/or their alkali metal or other salts, for example, sodium acetate, trifluoroacetate, beta-diketonates, acetylacetonate, propionate, butyrate, benzoate, or their corresponding acids; carboxylic acids and/or their alkali metal or other salts in a position alpha to a heteroaromatic nitrogen atom, such as, but not limited to, picolinic acid and substituted picolinic acids; picolinate and substituted picolinates, and their corresponding N-oxides. Suitable substituents for picolinic acid and picolinate include, but are not limited to, carboxylic acid, carboxylate, halogen, alkyl, heteroaryl, and aryl. Suitable beta-diketonates include those known in the art as ligands for the metal precursors of the present invention. Examples of beta-diketones (from which beta-diketonates are derived) include, but are not limited to, acetylacetone, benzoylacetone, dibenzoylmethane, diisobutyrylmethane, 2,2-dimethylheptane-3,5-dione, 2,2,6-trimethylheptane-3,5-dione, dipivaloylmethane, trifluoroacetylacetone, hexafluoroacetylacetone, benzoyltrifluoroacetone, pivaloyltrifluoroacetone, heptafluorodimethyloctanedione, octafluorohexanedione, decafluoroheptanedione, 4,4,4-trifluoro-1-phenyl-1,3-butanedione, 2-furoyltrifluoroacetone, 2-theonyltrifluoroacetone, 3-chloro-2,4-pentanedione, 3-ethyl-2,4-pentanedione, 3-methyl-2,4-pentanedione, methyl 4-acetyl-5-oxohexanoate. Mixtures of anionic ligand precursors are also within the scope of the invention. Metal complexes of the anionic ligands are also usable, e.g., VO(acetylacetonate)$_2$ and VO(picolinate)$_2$.

Suitable neutral, electron-donating ligand precursors include, but are not limited to, water; acetonitrile; nitrogen in a heteroaromatic ring, such as, but not limited to, pyridine, substituted pyridines, picolinic acid or substituted picolinic acids; alcohols; hydroxyaromatic compounds; phenol; substituted phenols; ethers; furan; tetrahydrofuran; phosphines; amines; amides; ketones; esters; Schiff bases; or imides. Mixtures of neutral, electron-donating ligand precursors are also within the scope of the invention.

The above precursors may be supplied to the solution separately or as metal complexes with at least one ligand. For example, one preferred formulation comprises the combination at low pH (e.g., less than about 4, and preferably less than about 3) of sodium metavanadate, a carboxylic acid, and a compound containing heteroaromatic nitrogen, e.g., picolinic acid, substituted picolinic acids, pyridine, substituted pyridines, or their corresponding N-oxides. Another preferred formulation comprises the combination of VO(acetylacetonate)$_2$ with a compound containing heteroaromatic nitrogen, e.g., a pyridyl compound. Still another combination comprises the combination of VO(picolinate)$_2$ with a carboxylate and/or a compound containing heteroaromatic nitrogen, e.g., a pyridyl compound. In each of the above formulations, the catalyst is formed in solution from a vanadium, niobium, or tantalum precursor; a carboxylic acid precursor (which may be in the form of a carboxylic acid or acid salt, or which may also function as the metal precursor); and a precursor compound containing heteroaromatic nitrogen, e.g., a pyridyl precursor (which may be in the form of the pyridyl compound itself, or which may also function as the metal precursor).

The stoichiometric ratio of the anionic ligand precursor to metal (i.e. vanadium, niobium, or tantalum, or mixture thereof) in the composition and stoichiometric ratio of the neutral, electron-donating ligand precursor to metal in the composition are not particularly limited so long as there is a sufficient molar quantity of anionic ligand and of neutral, electron-donating ligand to satisfy the vacant valency sites on the metal in the active catalyst species effective in the hydroxylation of an aromatic compound having at least one active aromatic hydrogen. In addition, the quantities of anionic ligand and neutral, electrondonating ligand are preferably not such that they interfere either with the hydroxylation reaction itself or with the isolation or purification of the product mixture, or with the recovery and reuse of catalyst components (such as metal).

When a ligand precursor is also a hydroxyaromatic compound produced by the reaction, then the stoichiometric ratio of ligand precursor to metal precursor may be directly related to the turnover number of the reaction, which is the yield of moles of product per moles of metal (or mixture of metals). The turnover number of the reaction determines the moles of hydroxyaromatic compounds produced. For optimum efficiency the turnover number is desired to be as high as possible. Preferred turnover numbers for the present invention are greater than 1, more preferably greater than about 10 and most preferably greater than about 50. Typically turnover numbers may be between about 5 and about 50.

In preferred embodiments of the present invention the stoichiometric ratio of both the anionic ligand precursor to metal and the neutral, electron-donating ligand precursor to metal in the composition are about 500-2: 1, more preferably about 100-2: 1, and still more preferably about 50-2: 1. When the catalyst composition comprises metal precusor (or mixture of metal precursors) in which the metal is supplied in the form of, for example, a complex with either the anionic ligand precursor, or the neutral, electron-donating ligand precursor, or both, then the stochiometric ratio of ligand precursor to metal is essentially 2:1, as for example in VO(acetylacetonate)$_2$ and in VO(picolinate)$_2$. It is also contemplated neutral, electron-donating ligand precursor, or both, may be added to the reaction mixture when the metal is supplied in the form of a complex with either the anionic ligand precursor, or both, may be added to the reaction mixture when the metal is supplied in the form of a complex with either the anionic ligand precursor, or the neutral, electron-donating ligand precursor, or both.

Without being bound by theory, it is hypothesized that suitable catalyst precursor combinations may give rise in the presence of molecular oxygen or a molecular oxygen precursor to catalysts having the general structure

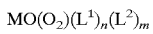
$$MO(O_2)(L^1)_n(L^2)_m$$

wherein M is a metal such as vanadium, niobium or tantalum; n is an integer from 0 to 1; m is an integer from 1 to 3; $L^1$ is an anionic, mono-or bi-dentate ligand; and $L^2$ is a neutral, electron-donating ligand Suitable anionic ligands include, but are not limited to, halides or the congugate base of a carboxylic acid, for example, acetate, trifluoroacetate, beta-diketonates, acetylacetonate, propionate, butyrate, benzoate, and the conjugate base of a carboxylic acid in a position alpha to a heteroaromatic nitrogen atom, such as, but not limited to, picolinate, and substituted picolinates, and their corresponding N-oxides. Suitable neutral, electron-donating ligands include, but are not limited to, water; acetonitrile; nitrogen in a heteroaromatic ring, such as, but not limited to, pyridine, pyridyl, picolinic acid or a substituted picolinic acid; alcohols; hydroxyaromatic compounds; phenol; substituted phenols; ethers; furan; tetrahydrofuran; phosphines; amine; amides; ketones; esters; Schiff bases; or imides.

The catalyst is present in an effective amount, which is readily determined empirically by one of ordinary skill in the art, depending on the starting aromatic substrate, the desired reaction rate, the cost of the catalyst, and like considerations. Generally, the catalyst will be present in amounts of up to about 10 mole percent of the aromatic substrate.

The reaction temperature is generally within the range of about 25° C. to about 200° C., preferably in the range of about 40° to about 150° C. Although the reaction time depends upon reaction conditions, the reaction time is generally several seconds to several hours.

Although the reaction may be run neat in benzene, toluene, or other aromatic substrate, at least one inert solvent may also be used where desirable to provide at least some degree of miscibility or microhomogeneity with respect to the catalyst, the aromatic substrate, oxygen and/or hydrogen. Solvents which enhance solubility and/or reactivity of the reactants are especially desirable, but the solvent will optimally solubilize, at least in part, the aromatic substrate, the catalyst, and oxygen and/or hydrogen without significantly decreasing the utilization efficiency of the catalyst. Exemplary solvents include, but are not limited to, acetonitrile, fluorinated hydrocarbons, freons, chloroform, dichloromethane, carbon tetrachloride, or combinations thereof.

Hydroxylation may be practiced either in a batch, semi-continuous, or continuous process. In a batch reaction catalyst and ligands are dissolved in the aromatic substrate or substrate/solvent mixture, preferably under an inert atmosphere, and a gaseous mixture comprising oxygen, hydrogen, and at least one inert gas is introduced into the reaction vessel. Although not necessary, it is preferred that the gas mixture be sparged or vigorously mixed with the reaction liquor in order to enhance transport into the liquor and thus increase reaction rate. In this instance, the use of a homogenous feedstock is advantageous in ensuring adequate contact between the catalyst and the aromatic substrate. The hydroxyaromatic compound or other products produced by the method of this invention may be separated and isolated by conventional techniques.

The following Examples are provided by way of example only, and should not be read to limit the scope of the invention.

EXAMPLE 1

0.01 grams (g) of VO(acetylacetonate)$_2$, 0.02 g of picolinic acid, and 50 milliliters (mL) of benzene were added to a stainless steel bomb. The bomb was sealed with a cap containing a gas-sparging stir shaft and reactor cooling coils. The reactor was then brought to 100° C. with stirring, and pressurized with 2.1% hydrogen gas in air at 6.9 MPa. Stirring was continued at this temperature and pressure for about 18 hours. The reaction was then cooled, and analysis by gas chromatography indicated the presence of 0.012 g of phenol and no other reaction products, indicating a turnover number (yield of moles of product per moles of catalyst) of 3.5.

EXAMPLE 2

VO(picolinate)$_2$ or catalyst precursors which in solution produce VO(O$_2$)(picolinate)(L)$_n$, (as described above) and benzene are added to a stainless steel bomb. The bomb is sealed with a cap containing gas-sparging stir shaft and reactor cooling coils. The reactor is then brought to reaction temperature (approximately 100° C.) with stirring, and pressurized with a mixture of hydrogen in air (approximately 6.9 MPa of 2.1% hydrogen gas). Stirring is continued at this temperature and pressure until no more gas uptake is observed. The reaction is then cooled, and analyzed by gas chromatography to show the presence of phenol in benzene.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A composition for hydroxylating an aromatic substrate having at least one active aromatic hydrogen, consisting of oxygen, hydrogen, and a catalyst formed in solution from a vanadium, niobium, or tantalum precursor or mixture thereof, at least one anionic ligand precursor, and at least one neutral, electron-donating ligand precursor.

2. The composition of claim 1, further comprising at least one inert gas.

3. The composition of claim 1, wherein the stoichiometric ratio of anionic ligand precursor to vanadium, niobium, or tantalum, or mixture thereof, and the stoichiometric ratio of neutral, electron-donating ligand precursor to vanadium, niobium, or tantalum, or mixture thereof are each about 500-2:1.

4. The composition of claim 1, wherein the stoichiometric ratio of anionic ligand precursor to vanadium, niobium, or tantalum, or mixture thereof, and the stoichiometric ratio of neutral, electron-donating ligand precursor to vanadium, niobium, or tantalum, or mixture thereof are each about 100-2:1.

5. The composition of claim 1, wherein the stoichiometric ratio of anionic ligand precursor to vanadium, niobium, or tantalum, or mixture thereof, and the stoichiometric ratio of neutral, electron-donating ligand precursor to vanadium, niobium, or tantalum, or mixture thereof are each about 50-2:1.

6. The composition of claim 1, wherein the anionic ligand precursor is at least one member selected from the group consisting of halides, carboxylic acids, acetic acid, trifluoroacetic acid, propionic acid, butyric acid, benzoic acid, beta-diketones, acetylacetone, conjugate bases of carboxylic acids, acetate, trifluoroacetate, propionate, butyrate, benzoate, beta-diketonates, acetylacetonate, carboxylic acids in a position alpha to a heteroaromatic nitrogen atom, picolinic acid, substituted picolinic acids, picolinic acid N-oxide, substituted picolinic acid N-oxides, conjugate bases of carboxylic acids in a position alpha to a heteroaromatic nitrogen atom, picolinate, substituted picolinates, picolinate N-oxide, and substituted picolinate N-oxides; and the neutral ligand precursor is at least one member selected from the group consisting of water, acetonitrile, nitrogen in a heteroaromatic ring, pyridine, substituted pyridines, picolinic acid, substituted picolinic acids, alcohols, hydroxyaromatic compounds, phenol, substituted phenols, ethers, furan, tetrahydrofuran, phosphines, amines, amides, ketones, esters, Schiff bases, and imides.

7. The composition of claim 1, wherein the catalyst is formed in solution from a vanadium, niobium, or tantalum precursor, or mixture thereof; a carboxylate precursor; and a pyridyl precursor.

8. The composition of claim 7, wherein the catalyst is formed in solution from a combination of picolinic acid and at least one of sodium metavanadate, VO(picolinate)$_2$ or VO(acetylacetonate)$_2$.

9. The composition of claim 1, wherein a catalyst in solution has the formula MO(O$_2$)(L$^1$)$_n$(L$^2$)$_m$, wherein M is vanadium, niobium or tantalum, n is an integer from 0 to 1, m is an integer from 1 to 3, L$^1$ is an anionic, mono- or bi-dentate ligand, and L$^2$ is a neutral, electron-donating ligand.

10. The composition of claim 9, wherein L$^1$ is at least one member selected from the group consisting of halides, conjugate bases of carboxylic acids, acetate, trifluoroacetate, beta-diketonates, acetylacetonate, propionate, butyrate, benzoate, conjugate bases of carboxylic acids in a position alpha to a heteroaromatic nitrogen atom, picolinate, substituted picolinates, picolinate N-oxide, and substituted picolinate N-oxides; and L$^2$ is at least one member selected from the group consisting of water, acetonitrile, nitrogen in a heteroaromatic ring, pyridine, substituted pyridines, picolinic acid, substituted picolinic acids, alcohols, hydroxyaromatic compounds, phenol, substituted phenols, ethers, furan, tetrahydrofuran, phosphines, amines, amides, ketones, esters, Schiff bases, and imides.

11. The composition of claim 1, wherein the aromatic substrate is benzene, naphthalene, anthracene, phenanthrene, or the foregoing substituted by at least one alkyl group, aryl group, hydroxyl, alkyl ether, aryl ether, or combinations thereof.

12. A composition for making phenol from benzene, comprising oxygen, hydrogen, and a catalyst formed in solution from a combination of picolinic acid, and at least one of sodium metavanadate, VO(picolinate)$_2$ or VO(acetylacetonate)$_2$.

13. The composition of claim 12, further comprising at least one inert gas.

* * * * *